(12) United States Patent
Singh

(10) Patent No.: US 11,200,306 B1
(45) Date of Patent: Dec. 14, 2021

(54) METHODS, DEVICES, AND SYSTEMS FOR AUTHENTICATING USER IDENTITY FOR LOCATION-BASED DELIVERIES

(71) Applicant: TELCOM VENTURES, LLC, Miami, FL (US)

(72) Inventor: Rajendra Singh, Indian Creek Village, FL (US)

(73) Assignee: TELCOM VENTURES, LLC, Miami, FL (US)

( * ) Notice: Subject to any disclaimer, the term of this patent is extended or adjusted under 35 U.S.C. 154(b) by 0 days.

(21) Appl. No.: 17/185,068

(22) Filed: Feb. 25, 2021

(51) Int. Cl.
| | |
|---|---|
| *G06F 21/00* | (2013.01) |
| *G06F 21/32* | (2013.01) |
| *H04L 29/06* | (2006.01) |
| *G06Q 50/26* | (2012.01) |
| *G06Q 20/40* | (2012.01) |

(Continued)

(52) U.S. Cl.
CPC ........... *G06F 21/32* (2013.01); *G06Q 10/083* (2013.01); *G06Q 20/40145* (2013.01); *G06Q 50/265* (2013.01); *H04L 63/0861* (2013.01); *H04L 63/126* (2013.01); *G06F 2221/2111* (2013.01); *G16H 10/60* (2018.01)

(58) Field of Classification Search
CPC ............ G06F 21/32; G06F 2221/2111; H04L 63/0861; H04L 63/126; G06Q 20/40145; G06Q 10/083; G06Q 50/265; G16H 10/60
See application file for complete search history.

(56) References Cited

U.S. PATENT DOCUMENTS

| | | |
|---|---|---|
| 5,243,652 A | 9/1993 | Teare et al. |
| 5,351,293 A | 9/1994 | Michener et al. |
| 6,119,096 A | 9/2000 | Mann et al. |

(Continued)

FOREIGN PATENT DOCUMENTS

| | | |
|---|---|---|
| CN | 106796710 A | 5/2017 |
| EP | 1470717 A2 | 10/2004 |

(Continued)

OTHER PUBLICATIONS

"Mobile Passport Control" published by Flysfo.com, 1 page (Jul. 18, 2015).

(Continued)

*Primary Examiner* — Jeffrey C Pwu
*Assistant Examiner* — William A Corum, Jr.
(74) *Attorney, Agent, or Firm* — Myers Bigel, P.A.

(57) ABSTRACT

A method for authenticating a user includes transmitting, from a first electronic device at a first location via a first communications link, first biometric information of a first user, authenticating a first identity of the first user for a transaction associated with an item, transmitting, from a second electronic device at a second location via a second communications link, second biometric information of a second user, authenticating a second identity of the second user located at the second location that is different from the first location, verifying that the first user at the first location corresponds to the second user at the second location, and authorizing access to the item at the second location, responsive to verifying by the server that the first user at the first location corresponds to the second user at the second location. Related systems, devices and computer program products are also described.

20 Claims, 8 Drawing Sheets

(51) Int. Cl.
  *G06Q 10/08* (2012.01)
  *G16H 10/60* (2018.01)

(56) References Cited

U.S. PATENT DOCUMENTS

| | | | |
|---|---|---|---|
| 6,985,588 B1 | 1/2006 | Glick et al. | |
| 7,120,254 B2 | 10/2006 | Glick et al. | |
| 7,143,289 B2 | 11/2006 | Denning et al. | |
| 7,194,273 B2 | 3/2007 | Vaudreuil | |
| 7,500,607 B2 | 3/2009 | Williams | |
| 7,512,989 B2 | 3/2009 | Scott | |
| 7,660,418 B2 | 2/2010 | Glick et al. | |
| 7,866,544 B1 | 1/2011 | Block et al. | |
| 8,064,378 B2 | 11/2011 | Karabinis | |
| 8,254,902 B2 | 8/2012 | Bell et al. | |
| 8,280,787 B1 | 10/2012 | Gandhi | |
| 8,328,094 B2 | 12/2012 | Proud et al. | |
| 8,438,066 B1 | 5/2013 | Yuen et al. | |
| 8,566,233 B2 | 10/2013 | Prakash et al. | |
| 8,604,901 B2 | 12/2013 | Hoyos et al. | |
| 8,626,194 B2 | 1/2014 | Busch | |
| 9,197,414 B1 | 11/2015 | Martin et al. | |
| 9,203,793 B2 | 12/2015 | Kandekar et al. | |
| 9,239,993 B2 | 1/2016 | Bergdale et al. | |
| 9,501,773 B2 | 11/2016 | Dai | |
| 9,661,216 B2 | 5/2017 | Tilt et al. | |
| 9,723,010 B2 | 8/2017 | Kerr | |
| 9,749,664 B1 | 8/2017 | Watson et al. | |
| 10,332,162 B1 | 6/2019 | Brock et al. | |
| 10,650,621 B1 | 5/2020 | King et al. | |
| 11,055,800 B2 | 7/2021 | Singh | |
| 2001/0016825 A1 | 8/2001 | Pugliese et al. | |
| 2003/0027551 A1 | 2/2003 | Rockwell | |
| 2003/0169881 A1 | 9/2003 | Niedermeyer | |
| 2003/0174049 A1 | 9/2003 | Beigel et al. | |
| 2004/0142658 A1 | 7/2004 | Mckenna et al. | |
| 2004/0169589 A1 | 9/2004 | Lea et al. | |
| 2005/0039208 A1 | 2/2005 | Veeck et al. | |
| 2005/0256724 A1 | 11/2005 | Rasin et al. | |
| 2006/0046746 A1 | 3/2006 | Ranford et al. | |
| 2006/0055512 A1 | 3/2006 | Chew | |
| 2006/0122729 A1* | 6/2006 | Murphy | G07F 5/18 |
| | | | 700/222 |
| 2006/0242027 A1 | 10/2006 | Falic | |
| 2006/0245620 A1 | 11/2006 | Roques et al. | |
| 2007/0046426 A1 | 3/2007 | Ishibashi | |
| 2007/0053306 A1 | 3/2007 | Stevens | |
| 2007/0055672 A1 | 3/2007 | Stevens | |
| 2007/0055785 A1 | 3/2007 | Stevens | |
| 2007/0233615 A1 | 10/2007 | Tumminaro | |
| 2008/0102956 A1 | 5/2008 | Burman et al. | |
| 2008/0102957 A1 | 5/2008 | Burman et al. | |
| 2008/0162346 A1 | 7/2008 | Aaron et al. | |
| 2008/0227434 A1 | 9/2008 | Nitta et al. | |
| 2008/0302870 A1 | 12/2008 | Berini et al. | |
| 2009/0042557 A1 | 2/2009 | Vardi et al. | |
| 2009/0098921 A1 | 4/2009 | Manning et al. | |
| 2009/0171842 A1 | 7/2009 | Blythe | |
| 2009/0204457 A1 | 8/2009 | Buhrmann et al. | |
| 2009/0215427 A1 | 8/2009 | Hawkins | |
| 2009/0251282 A1 | 10/2009 | Fitzgerald et al. | |
| 2010/0046553 A1 | 2/2010 | Daigle et al. | |
| 2010/0094693 A1 | 4/2010 | Corke | |
| 2010/0175001 A1 | 7/2010 | Lazarus et al. | |
| 2010/0198728 A1 | 8/2010 | Aabye et al. | |
| 2010/0308108 A1 | 12/2010 | Choi et al. | |
| 2011/0022517 A1 | 1/2011 | Hammad | |
| 2011/0066513 A1 | 3/2011 | Fournier et al. | |
| 2011/0091092 A1 | 4/2011 | Nepomniachtchi et al. | |
| 2011/0130885 A1 | 6/2011 | Bowen et al. | |
| 2011/0137804 A1 | 6/2011 | Peterson | |
| 2011/0177831 A1 | 7/2011 | Huang | |
| 2011/0179064 A1 | 7/2011 | Russo | |
| 2011/0288768 A1 | 11/2011 | Stefani et al. | |
| 2011/0313930 A1 | 12/2011 | Bailey | |
| 2012/0015622 A1 | 1/2012 | Kuz et al. | |
| 2012/0052787 A1 | 3/2012 | Zecha et al. | |
| 2012/0144458 A1 | 6/2012 | Mechaley | |
| 2012/0150686 A1 | 6/2012 | Aldomar et al. | |
| 2012/0166257 A1 | 6/2012 | Shiragami et al. | |
| 2012/0181333 A1 | 7/2012 | Krawczewicz et al. | |
| 2012/0203665 A1 | 8/2012 | Morgan et al. | |
| 2012/0330787 A1 | 12/2012 | Hanson et al. | |
| 2012/0330788 A1 | 12/2012 | Hanson et al. | |
| 2013/0079001 A1 | 3/2013 | Edara | |
| 2013/0091452 A1 | 4/2013 | Sorden et al. | |
| 2013/0117109 A1 | 5/2013 | Busch | |
| 2013/0160087 A1 | 6/2013 | Davis et al. | |
| 2013/0166340 A1* | 6/2013 | Salame | G06Q 10/06 |
| | | | 705/7.14 |
| 2013/0305059 A1 | 11/2013 | Gormley et al. | |
| 2013/0346310 A1 | 12/2013 | Burger et al. | |
| 2014/0018111 A1 | 1/2014 | Farley et al. | |
| 2014/0032346 A1 | 1/2014 | Hong et al. | |
| 2014/0156318 A1 | 6/2014 | Behun et al. | |
| 2014/0181927 A1* | 6/2014 | Sarkissian | H04L 63/0861 |
| | | | 726/6 |
| 2014/0244411 A1 | 8/2014 | Kim et al. | |
| 2014/0254693 A1 | 9/2014 | Mitchell et al. | |
| 2014/0278220 A1 | 9/2014 | Yuen | |
| 2014/0297067 A1 | 10/2014 | Malay | |
| 2014/0344011 A1 | 11/2014 | Dogin et al. | |
| 2014/0380501 A1 | 12/2014 | Niss | |
| 2015/0057925 A1 | 2/2015 | Schreiber | |
| 2015/0066797 A1* | 3/2015 | Outwater | G06Q 10/0833 |
| | | | 705/333 |
| 2015/0088619 A1 | 3/2015 | Larson et al. | |
| 2015/0096813 A1 | 4/2015 | Aumente | |
| 2015/0109428 A1 | 4/2015 | Mechaley | |
| 2015/0127536 A1 | 5/2015 | Van Den Broeck et al. | |
| 2015/0142612 A1 | 5/2015 | Hanna et al. | |
| 2015/0193764 A1 | 7/2015 | Haggerty et al. | |
| 2015/0242832 A1 | 8/2015 | Corritori et al. | |
| 2015/0296450 A1 | 10/2015 | Koo et al. | |
| 2015/0302409 A1 | 10/2015 | Malek et al. | |
| 2015/0373121 A1 | 12/2015 | Secilmis | |
| 2015/0380501 A1 | 12/2015 | Koshi et al. | |
| 2016/0048796 A1* | 2/2016 | Todasco | G06Q 10/083 |
| | | | 705/330 |
| 2016/0050203 A1 | 2/2016 | Hefetz | |
| 2016/0078397 A1* | 3/2016 | Barton | G06Q 20/382 |
| | | | 705/67 |
| 2016/0099905 A1 | 4/2016 | Kandekar et al. | |
| 2016/0148449 A1 | 5/2016 | God et al. | |
| 2016/0189096 A1 | 6/2016 | Tang et al. | |
| 2016/0286258 A1 | 9/2016 | Rajagopal et al. | |
| 2016/0343187 A1 | 11/2016 | Trani | |
| 2016/0352412 A1 | 12/2016 | Di Costanzo et al. | |
| 2016/0364559 A1 | 12/2016 | Bali et al. | |
| 2016/0368456 A1 | 12/2016 | Outwater et al. | |
| 2017/0063549 A1 | 3/2017 | Zwart et al. | |
| 2017/0068930 A1 | 3/2017 | Attar | |
| 2017/0161716 A1 | 6/2017 | Hurley et al. | |
| 2017/0180036 A1 | 6/2017 | Schaupmann et al. | |
| 2017/0193419 A1 | 7/2017 | Haparnas et al. | |
| 2017/0206345 A1 | 7/2017 | Lacous et al. | |
| 2017/0233098 A1 | 8/2017 | Gerard | |
| 2017/0262798 A1* | 9/2017 | Kosseifi | G08B 13/242 |
| 2017/0278156 A1 | 9/2017 | Parekh | |
| 2017/0302711 A1 | 10/2017 | Velayudhan et al. | |
| 2017/0372541 A1 | 12/2017 | Attar | |
| 2018/0007137 A1 | 1/2018 | Watson et al. | |
| 2018/0027037 A1 | 1/2018 | Watson et al. | |
| 2018/0027070 A1 | 1/2018 | Jhanji et al. | |
| 2018/0049250 A1 | 2/2018 | Perng et al. | |
| 2018/0098227 A1 | 4/2018 | Carnelli et al. | |
| 2018/0211527 A1 | 7/2018 | Ishihara et al. | |
| 2018/0234707 A1 | 8/2018 | Pujia et al. | |
| 2019/0035042 A1 | 1/2019 | Attar | |
| 2019/0095942 A1 | 3/2019 | Lee et al. | |
| 2019/0108690 A1 | 4/2019 | Mølmann et al. | |
| 2019/0148025 A1 | 5/2019 | Stone et al. | |
| 2019/0230212 A1 | 7/2019 | Spracklin et al. | |
| 2019/0356741 A1 | 11/2019 | Watson et al. | |

(56) References Cited

U.S. PATENT DOCUMENTS

| | | | |
|---|---|---|---|
| 2020/0042812 | A1 | 2/2020 | Sakaguchi et al. |
| 2020/0210951 | A1* | 7/2020 | Perez ................. G06Q 10/0838 |
| 2020/0265373 | A1* | 8/2020 | Koh .................. G06Q 30/0635 |
| 2021/0166257 | A1 | 6/2021 | Roeding et al. |
| 2021/0192656 | A1 | 6/2021 | Singh |

FOREIGN PATENT DOCUMENTS

| | | | |
|---|---|---|---|
| JP | 2002304376 A | 10/2002 | |
| JP | 2002335350 A | 11/2002 | |
| JP | 2004240725 A | 8/2004 | |
| JP | 2005122700 A | 5/2005 | |
| JP | 2007058469 A | 3/2007 | |
| JP | 2007088514 A | 4/2007 | |
| JP | 2008085977 A | 4/2008 | |
| JP | 2010212906 A | 9/2010 | |
| JP | 2012151735 A | 8/2012 | |
| JP | 2012531689 A | 12/2012 | |
| RU | 2716517 C2 | 3/2020 | |
| WO | 0035216 A1 | 6/2000 | |
| WO | 2012052787 A1 | 4/2012 | |
| WO | 2013163326 A1 | 10/2013 | |
| WO | 2017167568 A1 | 10/2017 | |
| WO | 2019112894 A1 | 6/2019 | |

OTHER PUBLICATIONS

Pozzebon, Alessandro "The PITAGORA project: Near field communication to improve passenger experience in airports" 2017 IEEE International Conference on RFID Technology & Application (RFID-TA) (pp. 63-68) (2017).
Rogers, Jason Lee "Authenticating airline passengers" IEEE Potentials 22(1):33-35 (Feb-Mar. 2003).
""Features" MamaBear App ©2012 Retrieved from URL: http://mamabearapp.com/features/ (2 pages) (retrieved Mar. 12, 2014)".
""Frequently Asked Questions" Textecution ©2014 Retrieved from URL: http://www.textecution.com/faqs.php (2 pages) (retrieved Mar. 12, 2014)".
"DUNCAN, Geoff "The Future of Digital Payments: Square Care Case, Google Wallet, and More" Digital Trends (3 pages) (Nov. 2, 2011)".
"LEE, Amy "Footprints iPhone App Lets You Track Your Kids, Spouse, Friends (PICTURES)" The Huffington Post (2 pages) (May 5, 2011)".
"Abstract—End-to-end passenger travel assistance from airport to airport with wearable device", Oct. 23, 2014, 1 p.
"Abstract—Notification and Communication System for Boarding Airlines using Passenger Real-Time Status and Location Telecommunication Services", Jun. 20, 2008, 1 p.
Bernal, Esteban , et al., "Onboard Condition Monitoring Sensors Systems and Techniques for Freight Railway Vehicles: A Review", IEEE Sensors Journal, vol. 19, No. 1, Jan. 1, 2019, pp. 4-24.
Groza, Bogdan , et al., "PRESTvO: PRivacy Enabled Smartphone based access To vehicle On-board units", IEEE Access, vol. 8, Jun. 19, 2020, 18 pp.
Herdiyanto, Dedy Wahyu, et al., "Passenger Authentication and Payment System Using RFID Based On-Board Unit for Surabaya Mass Rapid Transportation", 2016 International Seminar on Intelligent Technology and Its Applications (ISITIA), Jul. 28-30, 2016, Lombok, Indonesia, Jan. 20, 2017, pp. 305-310.
Li, Lin , et al., "Airborne Operation of Portable Electronic Devices", IEEE Antenna's and Propagation Magazine, vol. 44, No. 4, Aug. 2002, pp. 30-39.
Narzt, Wolfgang , et al., "Be-In/Be-Out with Bluetooth Low Energy: Implicit Ticketing for Public Transportation Systems", 2015 IEEE 18th International Conference on Intelligent Transportation Systems, Proceedings, ITSC, Sep. 15-18, 2015, Gran Canaria, Spain, Oct. 30, 2015, pp. 1551-1556.
Restrepo-Calle, Felipe , et al., "A Vehicle Tracking Device With Built-in Safety Features for Public Transportation Systems", 2019 2nd Latin American Conference on Intelligent Transportation Systems (ITS LATAM), Mar. 19-20, 2019, Bogota Colombia, Mar. 19, 2019, 6 pp.
Sampigethaya, Krishna, et al., "Aviation Cyber-Physical Systems: Foundations for Future Aircraft and Air Transport", Proceedings of the IEEE, vol. 101, No. 8, Aug. 2013, pp. 1834-1855.
Sampigethaya, Krishna, et al., "Secure Operation, Control, and Maintenance of Future E-Enabled Airplanes", Proceedings of the IEEE, vol. 96, No. 12, Dec. 2008, pp. 1992-2007.
Shaikh, Farooq , et al., "A Review of Recent Advances and Security Challenges in Emerging E-Enabled Aircraft Systems", IEEE Access, vol. 7, May 2019, pp. 63164-63180.
STIC , "EIC 3600 Search Report", dated Jul. 13, 2021, 12 pp.
STIC , "EIC Search Report", dated Sep. 15, 2021, 20 pp.
Strauss, Bill , et al., "Unsafe at Any Airspeed?", IEEE Spectrum, vol. 43, Issue 3, Mar. 2006, pp. 44-49.
Zimmerman, Thomas , et al., "Travel Card: Airport Self-Check In Using a Wireless PDA", 2001 IEEE Intelligent Transportation Systems Conference Proceedings, Aug. 25-29, 2001, Oakland, CA, Oct. 22, 2001, pp. 1224-1228.

\* cited by examiner

810 — TRANSMITTING, RESPONSIVE TO THE INDICATION THAT THE IDENTIFICATION DOCUMENT BEING ACCEPTED, BIOMETRIC IDENTIFICATION INFORMATION OF THE USER FOR STORING AT THE SERVER

FIG. 8

910 — DETERMINING THAT THE SECOND USER AT THE SECOND LOCATION IS DIFFERENT FROM THE FIRST USER AT THE FIRST LOCATION

920 — DETERMINING IF THE SECOND USER IS AN AUTHORIZED RECIPIENT DESIGNATED BY THE FIRST USER

930 — AUTHORIZING ACCESS TO THE ITEM BY THE SECOND USER AT THE SECOND LOCATION, RESPONSIVE TO DETERMINING THAT THE SECOND USER IS THE AUTHORIZED RECIPIENT DESIGNATED BY THE FIRST USER

FIG. 9

1010 — RECEIVING AN INDICATION FROM THE FIRST USER INDICATING AN IDENTIFICATION OF THE SECOND USER AS THE AUTHORIZED RECIPIENT

FIG. 10

STORING, IN A DATABASE, A CERTIFICATE ASSOCIATED WITH THE TRANSACTION AND BIOMETRIC INFORMATION OF THE FIRST USER, RESPONSIVE TO THE TRANSACTION BY THE FIRST USER ⎯1310

FIG. 13

RETRIEVING, THE CERTIFICATE AND THE BIOMETRIC INFORMATION OF THE FIRST USER FROM THE DATABASE, WHEN THE FIRST USER ATTEMPTS TO AUTHENTICATE AT THE SECOND LOCATION ⎯1410

VERIFYING IF THE BIOMETRIC INFORMATION OF THE FIRST USER FROM THE DATABASE MATCHES WITH BIOMETRIC INFORMATION OF THE FIRST USER COLLECTED AT THE SECOND LOCATION ⎯1420

PROVIDING ACCESS TO THE CERTIFICATE, RESPONSIVE TO VERIFYING THAT THE BIOMETRIC INFORMATION OF THE FIRST USER FROM THE DATABASE MATCHES WITH BIOMETRIC INFORMATION OF THE FIRST USER COLLECTED AT THE SECOND LOCATION ⎯1430

FIG. 14

DETERMINING A COST OF THE ITEM BASED ON THE SECOND LOCATION ASSOCIATED WITH DELIVERY OF THE ITEM ⎯1510

PROVIDING THE COST TO THE FIRST USER UPON DELIVERY OF THE ITEM ⎯1520

FIG. 15

METHODS, DEVICES, AND SYSTEMS FOR AUTHENTICATING USER IDENTITY FOR LOCATION-BASED DELIVERIES

FIELD

Various embodiments described herein relate to user authentication, and more specifically to user authentication for location-based deliveries.

BACKGROUND

Many jurisdictions have rules where goods shipped in or out of the jurisdiction may be subjected to restrictions or taxes. Examples of activities that are exempt from such jurisdiction-based taxes include duty free shopping, which is applicable when a person is travelling from one country to another. Other examples of a jurisdiction-based restriction are that a person may need to be a certain age if particular goods are to be delivered to them, or the person who accepts delivery of particular goods needs to be authorized by the person who purchased the goods to be delivered. The goods may be moved from location A to location B after the purchase has occurred. The jurisdiction or location may be countries, states, counties, or particular geofenced areas.

SUMMARY

Various embodiments of the present inventive concepts include a method for authenticating a user. The method includes authenticating a first user located at a first location for a transaction associated with an item, authenticating a second user located at a second location that is different from the first location, verifying that the first user at the first location corresponds to the second user at the second location, and authorizing access to the item at the second location, responsive to verifying that first user at the first location corresponds to the second user at the second location.

According to some embodiments, authenticating the first user may include obtaining first biometric information of the first user using a first device at the first location, and authenticating the second user may include obtaining second biometric information of the second user using a second device at the second location. The first biometric information and the second biometric information each may include one or more of fingerprinting, retina scans, iris recognition, facial recognition, voice identification, or finger vein identification.

According to some embodiments, verifying that the first user at the first location corresponds to the second user at the second location may include determining that first authentication information associated with the first user corresponds to second authentication information associated with the second user, and identifying that the second user is same as the first user, responsive to the first authentication information corresponding to the second authentication information.

According to some embodiments, the method may include determining that the second location corresponds to a delivery location established at a time of the transaction, and delivering the item to the delivery location, responsive to the authorizing access to the item. The method may include, prior to the transaction, transmitting a scan of an identification document of the user to a server that communicates with a validation agency, and receiving, from the server, an indication that the identification document has been accepted. The method may further include transmitting, responsive to the indication that the identification document being accepted, biometric identification information of the user for storing at the server. The biometric identification information may be used for authenticating the first user and/or for authenticating the second user.

According to some embodiments, the method may include determining that the second user at the second location is different from the first user at the first location, determining if the second user is an authorized recipient designated by the first user, and authorizing access to the item by the second user at the second location, responsive to determining that the second user is the authorized recipient designated by the first user. The method for authenticating the user may include receiving an indication from the first user indicating an identification of the second user as the authorized recipient. Authorizing access to the item may include determining if the item is a restricted delivery item, comparing one or more parameters of the second user corresponding to one or more restriction parameters associated with the restricted delivery item, and authorizing access to the item, responsive to the comparing the one or more parameters of the second user with the one or more restriction parameters associated with the restricted delivery item.

According to some embodiments, the delivery of the item is authorized if the second location of the second user is within a predetermined proximity of a delivery location established at a time of the transaction. The delivery of the item may be authorized for a specific time window. Authenticating the second user may include receiving, by the second user, a request from a delivery representative to provide biometric information, providing by the second user, the biometric information requested by the delivery representative, and verifying that the biometric information provided by the second user corresponds to stored biometric information that was stored in a server that is remote from the second user.

According to some embodiments, the first user may be the same as the second user. The method may include storing, in a database, a certificate associated with the transaction and biometric information of the first user, responsive to the transaction by the first user. The method may include retrieving the certificate and the biometric information of the first user from the database when the first user attempts to authenticate at the second location, verifying if the biometric information of the first user from the database matches with biometric information of the first user collected at the second location, and providing access to the certificate, responsive to verifying that the biometric information of the first user from the database matches with biometric information of the first user collected at the second location. The certificate may include a proof of vaccination, a prescription for a medication, and/or an authorization to carry the medication. A cost of the item may be determined based on the second location associated with delivery of the item. The cost may be provided to the first user upon delivery of the item.

According to some embodiments, a wireless electronic device may be configured to perform the operations described herein. According to some embodiments, a computer program product may include a non-transitory computer readable storage medium comprising computer readable program code therein that when executed by a processor causes the processor to perform operations described herein.

According to some embodiments, a wireless electronic device for authenticating a delivery of an item may include a transceiver configured to perform operations including receiving first biometric information of a user located at a first location corresponding to a transaction location associated with the item, and receiving second biometric information of the user located at a second location corresponding to a delivery location. The wireless electronic device may include one or more processors configured to perform operations including verifying that the first biometric information of the user at the first location corresponds to the second biometric information of the user at the second location, and authorizing access to the item at the second location, responsive to verifying that first biometric information corresponds to the second biometric information.

According to some embodiments, a system may include a server and a first wireless electronic device that includes a first processor configured to collect first biometric information of a user located at a first location for a transaction associated with an item, and a first transceiver configured to transmit the first biometric information from the wireless electronic device to the server. The system may include a second wireless electronic device that includes a second processor configured to collect second biometric information of the user located at a second location that is different from the first location, and a second transceiver configured to transmit the second biometric information from the wireless electronic device to the server. The server is configured to perform operations including verifying that the first biometric information of the user at the first location corresponds to the second biometric information of the user at the second location, and authorizing access to the item at the second location, responsive to verifying that first biometric information corresponds to the second biometric information.

According to some embodiments, authenticating the first user may include transmitting first biometric information of a first user for a transaction associated with an item from a first electronic device at a first location via a first communications link. A first indication that the first user has been biometrically authenticated may be received at the first electronic device via the first communications link. Second biometric information of a second user may be transmitted from a second electronic device at a second location via a second communications link. A second indication that the second user has been biometrically authenticated may be received at the second electronic device via the second communications link. A verification indication from a server that the first user at the first location corresponds to the second user at the second location may be received at the second electronic device. Access to the item at the second location may be authorized, responsive to receiving the verification indication from the server.

It is noted that aspects of the inventive concepts described with respect to one embodiment, may be incorporated in a different embodiment although not specifically described relative thereto. That is, all embodiments and/or features of any embodiment can be combined in any way and/or combination. Other operations according to any of the embodiments described herein may also be performed. These and other aspects of the inventive concepts are described in detail in the specification set forth below.

BRIEF DESCRIPTION OF THE DRAWINGS

The accompanying drawings are included to provide a further understanding of the present disclosure and are incorporated in and constitute a part of this application. These drawings illustrate certain example embodiments. In the drawings:

FIGS. 2 to 15 are flowcharts of operations for authenticating a user in the system of FIG. 1, according to various embodiments described herein.

DETAILED DESCRIPTION

Various embodiments will be described more fully hereinafter with reference to the accompanying drawings. Other embodiments may take many different forms and should not be construed as limited to the embodiments set forth herein. Like numbers refer to like elements throughout.

Secure authentication of a user making a transaction or purchase and/or receiving delivery of an item is needed for geographically remote distribution networks and/or for contactless transactions. Different jurisdictions related to the location of an order or a purchase and the location of a delivery or receipt of the order may have different rules that govern the transactions. The present inventive concepts arise from the recognition that a combination of authentication at a first jurisdiction in a location or geofenced area and authentication at a second jurisdiction that is in a different location from the previous geofenced location are needed for secure transactions. Authentication may include biometric authentication of the user and/or delivery recipient. In some embodiments, authentication may include password-based authentication, multi-factor authentication, certificate-based authentication, and/or token based authentication. In some embodiments, two or more types of authentication may be combined. For example, biometric authentication may be combined with another method of authentication before authenticating the user and authorizing delivery.

Figure 1:
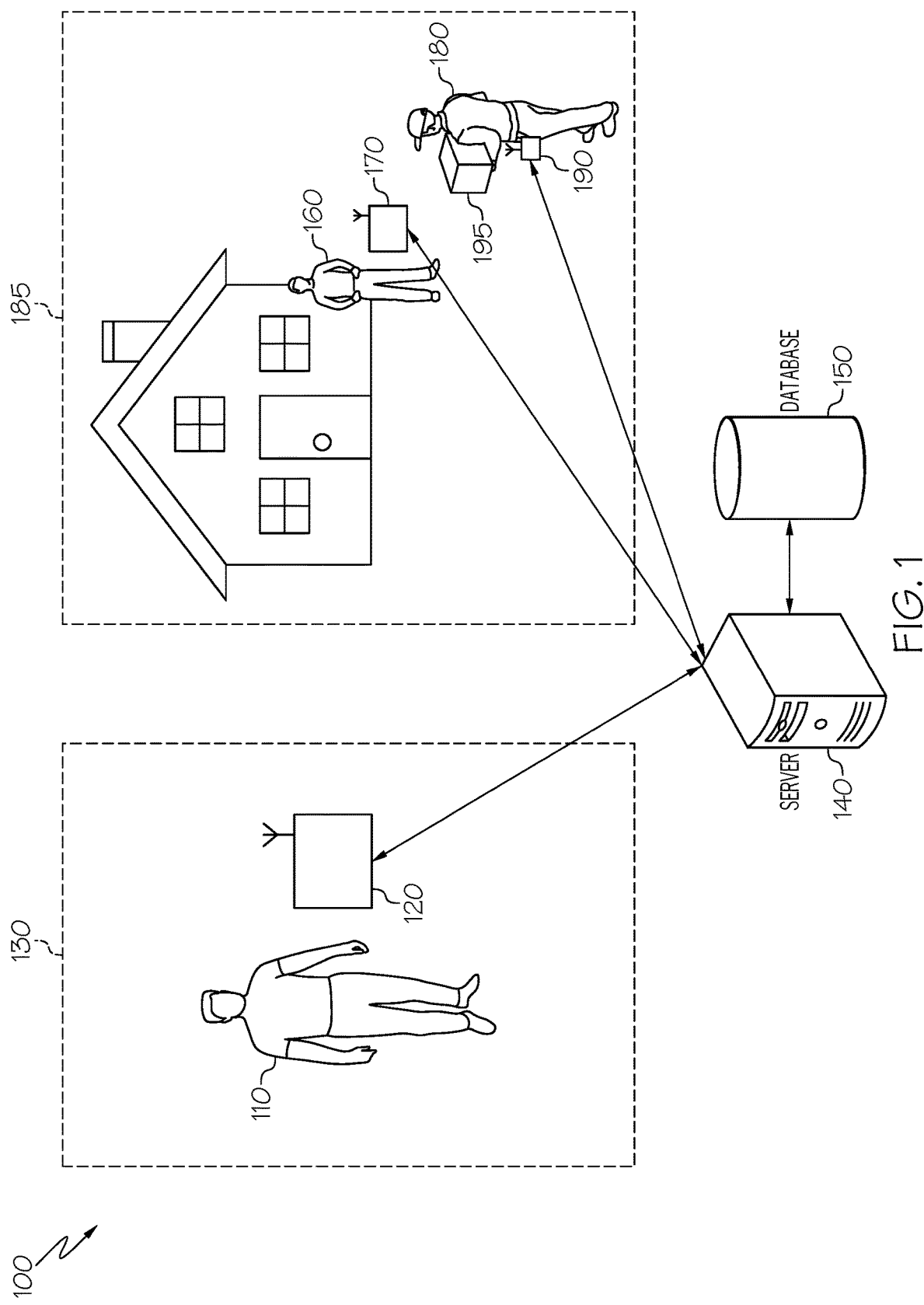
FIG. 1 is a diagram of a system for authenticating a user, according to various embodiments described herein.

FIG. 1 is a diagram of a system for authenticating a user. Referring to FIG. 1, system 100 may include a server 140 that is connected to a database 150. The server 140 is configured to authenticate a user for a transaction such as a purchase of an item, a subscription, vaccination, or prescription. A user 110 in a geographic area or location 130 may be involved in a transaction. The user 110 may provide information such as biometric information to a terminal 120. Terminal 120 may be a wireless device connected over a network to a server 140 that provides authentication. The biometric information provided by the user 110 may be stored by the server 140 into an associated database 150. In a second geographical area or location 185, a user 160 may provide information such as biometric information to a terminal 170. The user 160 may be the same as user 110 that performed the transaction at location 130. In other words, user 110 may have traveled from geographic area or location 130 to geographic area or location 185. In some embodiments, the user 160 may be a different user designated by user 110. The information may be transmitted from terminal 170 to the server 140 for verification. The server 140 may communicate with a terminal 190 associated with delivery representative 180. Upon receiving authorization for delivery, the delivery representative 180 may deliver item 195 to user 160. The terminal 190 may receive the authorization for delivery if it is in proximity of terminal 170. Proximity of terminal 170 to terminal 190 may be determined based on both devices being within the geographical area or location 185. In some embodiments, proximity of terminal 170 to terminal 190 may be determined based on communication such as near-field communication (NFC) or BLUETOOTH® between the devices. According to some embodiments, the user 160 may provide the authentication information such as biometric information directly to the terminal 190 of the delivery representative 180. Delivery representative 180 may be a person that brings the ordered item to the user 160. In some embodiments, the delivery representative 180 may be a drone, a vehicle, or automated vehicle that carries the item for delivery.

Prior to initiating transactions from the user, a setup operation may be performed in which the user establishes a profile and/or an account with a vendor or supplier. The setup process may include verifying the user's information such as age, citizenship, etc. by identification documents. These identification documents may, for example, be scanned via an application on a terminal or mobile device and verified remotely or by Artificial Intelligence (AI) in order to complete the account profile. This verification may be part of a sign up or registration process. Identification documents such as a driver's license or passport may be verified by recognizing portions of a scan or an image of the identification document, or by validating watermarks or other symbols in the identification document. In some embodiments, a scan or image of the identification document may be sent to a server at a validation agency or government agency that verifies and validates the document and/or identifying information. The server at the validation agency or government agency may send an indication to the vendor or server associated with the vendor that the identification document is valid. Upon verification, the information may be stored securely in an application database and/or vendor server so that this verification and/or identification process do not have to be repeated with each transaction and/or delivery. Thereafter, the application may verify the user via biometric identification such as fingerprinting, retina scans, iris recognition, facial recognition, voice identification, finger vein identification, etc. The biometric identification may be performed at a terminal or device at the location of the sale or order for goods or services. The biometric identification of the user may be validated locally at the terminal or device or related information may be sent to a secure server that validates the biometric identification. Biometric identification may also be used at the point of delivery or pickup of the purchased goods or services.

An authentication, such as biometric authentication, may be done by an application or other program on a terminal or mobile device at the time a person (or a business entity) places the order for the goods or services to be delivered. In some embodiments, the biometric authentication may be performed at a server that receives the biometric information collected from sensors associated with the terminal or mobile device. The location of the user may be stored in the terminal or device at the point of sale and/or in a database that is remote from the terminal or place of business. A unique order number may be assigned to the user that placed the order.

When a person such as the user that placed the order or a designated pick up person arrives in a location (i.e., different jurisdiction) where goods are to be delivered, applicable rules are checked related to the specific goods that are to be shipped or delivered. The user may be requested for the biometric information by an application running on a terminal at the pick-up location or on a mobile device associated with the user. If the biometric authentication matches with the authentication at the time or sale or order, and/or the location matches with the location (jurisdiction) of where the goods are supposed to be delivered, then the goods or services may be cleared for delivery.

Upon completing biometric authentication, goods may be delivered to a location (i.e., jurisdiction) which was identified at the time of sale or order. The delivery of the goods or services also may be accepted by a person who has the unique code or order number assigned at the time of order or purchase and/or meets the criteria to accept the goods (such as age, location, etc.). If the authorized recipient of goods is within proximity, goods can be delivered without a physical signature, thereby providing contactless delivery.

The present inventive concepts provide authentication of a person who purchased an item or service, verification that the same person or their designated agent moved from the location of purchase to a point of delivery or receipt of the item or service, and/or verification of physical location of the purchase and/or delivery. The different locations of the point of purchase and the point of delivery or receipt of the goods or services may be of importance in view of regulatory laws, trafficking laws, tax structure, and/or duty-free concessions associated with particular jurisdictions.

For example, regulatory laws may restrict the purchase of items such as guns, alcohol, marijuana, etc. These regulatory laws may be jurisdiction specific such that sales may be allowed in some townships, counties, states, or countries, but restricted in other areas. Trafficking laws may prevent, for example, making or selling goods in some jurisdictions and transferring these goods for sale in a different jurisdiction such as, for example, across state lines. Tax laws and duties that are imposed may vary in different jurisdictions. For example, a person that works and shops in New York, but resides in New Jersey, may pay taxes at the New Jersey tax rate on goods purchased in New York, but delivered to their residence in New Jersey. At the time and/or location of sale, the user's profile may indicate their residence and/or associated tax rate for New Jersey. The user may also manually indicate their residence/delivery jurisdiction at a terminal or mobile device on which an order or sale is placed. At the pickup or delivery of the goods or services, the user and/or the location may be authenticated in order to apply the proper tax rate that should be charged. In some cases, items may be designated as being duty-free if the user purchases in a first location and then receives the items or services at a second location.

The sale and/or delivery of items such as alcohol may be regulated in terms of time of sale, time of delivery, quantity of purchase, and/or verification of age of the purchaser and/or the delivery recipient. Conventional delivery of regulated items may require a signature from the recipient. Obtaining a signature by a delivery company may be inconvenient since it requires the recipient to be home at the time that the delivery representative attempts the delivery. Additionally, obtaining a signature typically includes interaction between the delivery representative and the recipient, which may not be desirable due to health and other concerns.

According to various embodiments described herein, a verification or authentication of the recipient may be performed by a terminal or other device using biometric authentication to determine if the purchaser or designated recipient is indeed an authorized recipient. The authentication may include determining if the recipient has been in the proximity of the designated delivery location (i.e., a geo-fenced area) within a period of time prior to the delivery. For example, a mobile device of the delivery recipient may indicate to a server accessible by the delivery company that the delivery recipient was in the house or building at the delivery address within the previous 12 hours of the attempted delivery. If the location of the user's mobile device has been in the delivery location within a threshold amount of time, the delivery may be authorized.

Specifically, the delivery recipient may have been within the geo-fenced area including the delivery address until 8:00 am, at which time they left to travel to their work location. The delivery recipient may log into an application on their mobile device, provide biometric authentication information, and authorize delivery of the package that day. In some embodiments, the recipient may need to verify their age or enter a code provided at the time of purchase in order to authenticate the delivery, in addition to providing the biometric information. A delivery representative may arrive four hours later, at 12:00 pm, to attempt to deliver the package. Upon arrival at the delivery location, the delivery representative may receive a notification that the recipient was authenticated and within the proximity during the last 12 hours. Therefore, the recipient is authenticated and the delivery representative may leave the package at the location since the recipient was authenticated based on their identity and their location. The delivery representative may be a person representing the vendor or a delivery company, or may be a drone that is configured to deliver packages based on various conditions described herein.

In some embodiments, the delivery may be completed only if the present location of the recipient is within a specified distance from the delivery location. For example, if the recipient is within five miles of the delivery location, such as at a local grocery store, gym, or workplace, the delivery may be authorized. However, if the recipient is farther than the specified distance, such as having traveled outside of the city or state, the delivery may not be authorized. In this case, the biometric authentication, the recent location of the recipient, and the present location of the recipient may be considered when authorizing the delivery.

According to some embodiments, timestamps may be used for various activities within the sale of an item or service. Various timestamps may be associated with the time of sale, the time of the recipient entering or leaving the delivery location, and/or the time of delivery. These timestamps may be compared to determine if delivery is authorized. For example, delivery of a perishable item such as milk may need to occur within a specific amount of time before the perishable item spoils. If the delivery representative arrives after the time window for delivery, the delivery may not be authorized and thus canceled. In some cases, the timestamps may be compared to provide a waiting period between purchase and delivery of the item. For example, many states have laws that require a waiting period before obtaining possession of a firearm. In this case, the timestamp at the time of purchase may be compared with the timestamp at the time of arrival of the delivery representative at the delivery location. If the delivery timestamp indicates that a sufficient amount of time has elapsed, then the item may be authorized for delivery. In some embodiments, the timestamps may be used to determine a price, bonus, or tip amount. For example, if the timestamp associated with the delivery is within a specific time period from the timestamp of the order being placed, the delivery may trigger payment of a bonus or a larger tip.

The timestamps and biometric authentications of the user may also be used in conjunction with the location at the purchase point and the location at delivery to determine if the same user traveled from one jurisdiction to another, thereby entitling them to a duty-free purchase. The server may also track the purchases of the user and limit or restrict the amounts of purchases allowed. For example, a particular user may be restricted from buying certain items due to age, or may be restricted to purchase of a limited amount of an item such as alcohol or marijuana. The biometric authentication at the purchase point may be used to track purchases by a particular user at a server, such that these limitations may be imposed on purchases and/or on deliveries.

Public safety or government agencies may be able to place restrictions on certain persons based on their biometric authentication. For example, purchase and/or delivery of particular items may be restricted on particular days or times based on the user profile and/or biometric data. For example, a user listed as a felon may not be allowed to take delivery of firearms but may be able to obtain other restricted items such as alcohol.

According to some embodiments, the order transaction or purchase are tied to authenticating a specific person, and thus the ability to receive the delivery is tied to the same physical person. The same person may need to be present for the purchase of the item or service and may also need to be present to receive delivery.

Some embodiments of the present inventive concepts may be applied to the healthcare industry, such as for a person receiving medications or vaccinations. A user may receive a vaccination, medication, or treatment at a healthcare provider. Biometric authentication at the point of medical service may validate that the given user indeed received the vaccination or other treatment, particularly when verification of vaccination is needed if they travel to another location. The user may be validated at the clinic as a particular user. A certificate of vaccination or treatment may be stored along with the biometric information of the user captured at the healthcare facility location. The certificate of vaccination may be stored on the user's mobile device and/or at a remote server. Location information may also be stored, in addition to the certificate and biometric information. The location where the biometric information is collected may be used to validate that the vaccination and/or related certificate were obtained at a valid healthcare facility location. When traveling, the user may be required to show proof of vaccination. Biometric information may be collected at the airport or at the travel destination and be used to validate that the particular traveler has indeed been vaccinated. The biometric information collected at the airport or travel destination may be compared with the biometric information captured at the healthcare facility to ensure that the same user had obtained the vaccination.

Similar concepts may be applied to provide authentication for the receipt or transport of medications. When a user is examined at a healthcare facility and obtains a prescription, they may be authenticated. Biometric information of the user, along with prescription information, may be stored at a server. The user may then go to a pharmacy or other medical dispensary at a location that is separate from the healthcare facility. The prescription record may be retrieved from the server. The user may then be biometrically authenticated to ensure that the same person that was seen in the healthcare facility and received the prescription is the one trying to obtain the medication. Similarly, a person in possession of a medicine may be traveling to a location that restricts the transport and use of that medicine. Upon arrival at the new location, the person may be authenticated by a device to verify against information stored at a server that the same person in possession of the medication has traveled. The biometric information of the person and the medication may be compared with the biometric information and prescription stored in the server.

Figure 2:
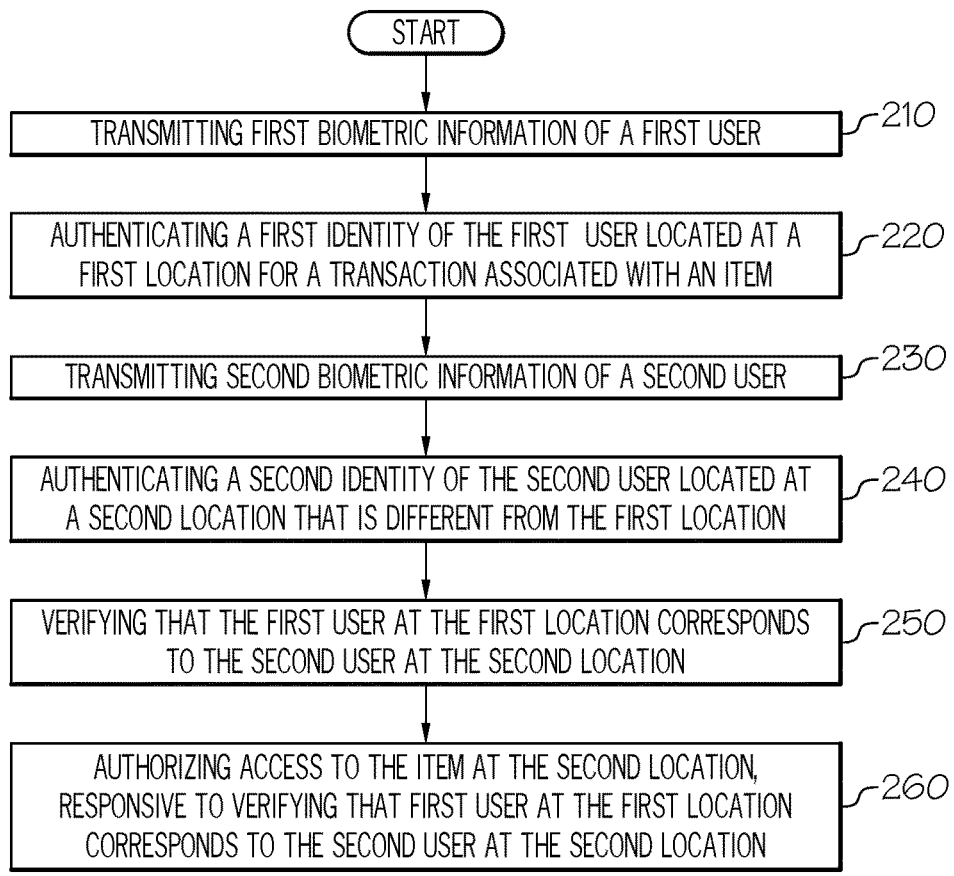

FIG. 2 is a flowchart of operations according to some embodiments of the present inventive concepts. Referring now to FIG. 2, first biometric information of a first user may be transmitted from a first electronic device at a first location via a first communications link, at block 210. The first biometric information may be transmitted to a server over a communication network. A first identity of the first user located at a first location may be authenticated for a transaction associated with an item, at block 220. Specifically, the user may provide information such as biometric information to a terminal used for the transaction. For example, the terminal may be a mobile device of the user or a terminal in a place of business such as a shop or kiosk. The terminal may include one or more cameras and/or biometric sensors to collect biometric information such as fingerprinting, retina scans, iris recognition, facial recognition, voice identification, or finger vein identification. Access to the terminal may be locally authenticated. However, authenticating the transaction may occur over a network by communicating with a server. In other words, biometric information provided to sensors at the terminal may be transmitted to a server that is remote from the terminal. The server may authenticate the transaction using information such as the biometric information provided at the terminal. This authentication at the transaction location (i.e., the geographical area in which the transaction is taking place) may be confirmed by the server, which then sends an indication back to the terminal at the transaction location to allow the transaction such as the order or purchase to be completed. Second biometric information of a second user may be transmitted from a second electronic device at a second location via a second communications link, at block 230. The second biometric information may be transmitted to the server over the communication network.

Still referring to FIG. 2, a second identity of the second user located at a second location that is different from the first location may be authenticated, at block 240. Authentication may include confirming that biometric information collected from the user matches that stored with an associated profile of the user. The second user, in some embodiments, may be the same as the first user that was authenticated in the first location. A terminal at the second location, which may include a mobile device of the user and/or a device of the delivery representative, may include one or more cameras and/or biometric sensors to collect biometric information. This information is sent from the mobile device of the user and/or the device of the delivery representative to a server for authentication. This authentication at the delivery location (i.e., the geographical area in which delivery is to occur) may be confirmed by the server. In some embodiments, the server may send an indication back to the terminal of the user and/or the terminal of the delivery representative at the delivery location indicating that the user has been authenticated as being the person that was expected as stored in the database associated with the server. The server may verify that the first user at the first location corresponds to the second user at the second location, at block 250. The server may compare the biometric information provided by the user at the first location with the biometric information provided by the user at the second location. In some embodiments, the server may also verify that both of these pieces of biometric information correspond to that saved in a user profile. The server may verify that the same person was at the original transaction location that was at the delivery location. The server may provide an indication that authorizes access to the item at the second location, responsive to verifying that first user at the first location corresponds to the second user at the second location, at block 260. The authorization indication from the server to the delivery representative may allow delivery of the item to be completed. In some embodiments, the item that was purchased or rented may not need a physical delivery representative. Items such as internet content such as movies may be provided to the user's device once biometric verification takes place that the same user or authorized user is attempting to receive the content that was purchased or rented.

Figure 3:
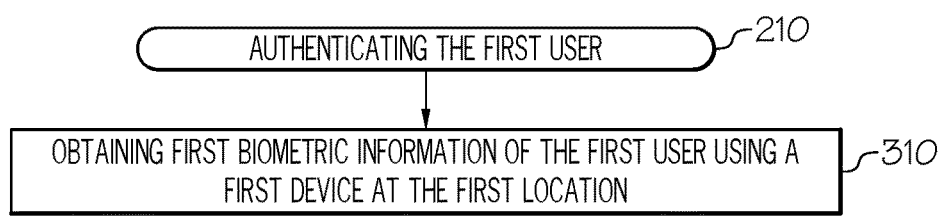
Figure 4:
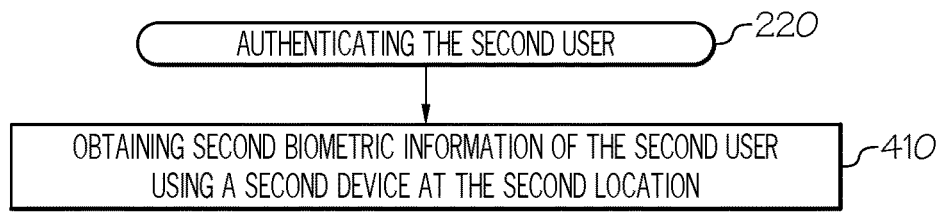

FIGS. 3 and 4 are flowcharts of operations according to some embodiments of the present inventive concepts. Referring now to FIG. 3, authenticating the first user may include obtaining first biometric information of the first user using a first device at the first location, at block 310. Referring now to FIG. 4, authenticating the second user may include obtaining second biometric information of the second user using a second device at the second location, at block 410. The first biometric information and the second biometric information may each be one or more of fingerprinting, retina scans, iris recognition, facial recognition, voice identification, finger vein identification, or other data associated with a person.

Figure 5:
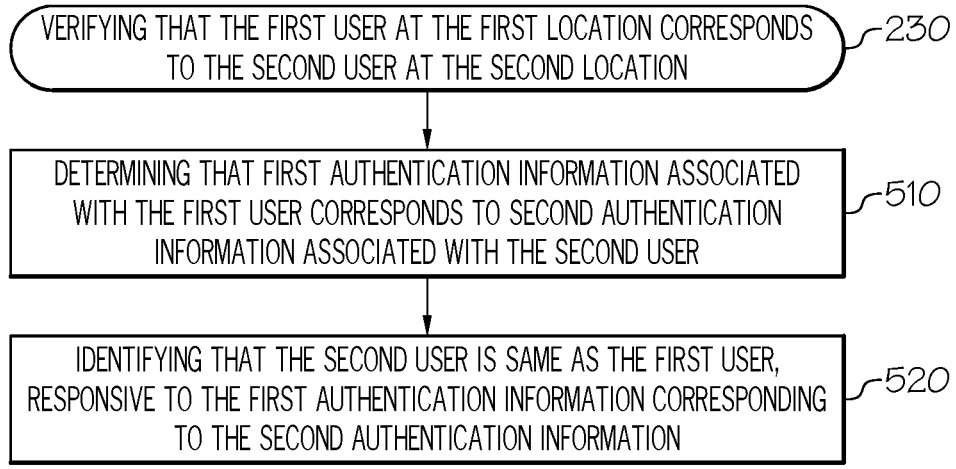

FIG. 5 is a flowchart of operations according to some embodiments of the present inventive concepts. Referring now to FIG. 5, verifying that the first user at the first location corresponds to the second user at the second location may include determining that first authentication information associated with the first user corresponds to second authentication information associated with the second user, at block 510, and identifying that the second user is same as the first user, responsive to the first authentication information corresponding to the second authentication information, at block 520. This verification may take place at the server. The server may compare the biometric information sent by the user from the first location and the biometric information subsequently sent by the user from the second information. If the biometric information indicates that the same user has been authenticated at both locations, then the server indicates the verification. An exact match of the biometric information may not be necessary such that a match within a tolerance level may be determined to be sufficient for verification.

Figure 6:
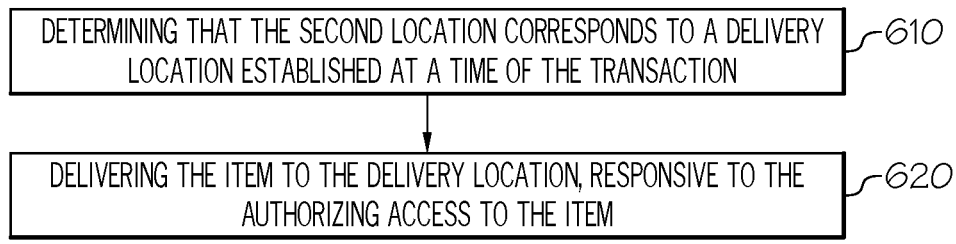

FIG. 6 is a flowchart of operations according to some embodiments of the present inventive concepts. Referring now to FIG. 6, a determination may be made that the second location corresponds to a delivery location established at a time of the transaction, at block 610. The item may be delivered to the delivery location, responsive to the server authorizing access to the item, at block 620.

According to some embodiments, a time associated with the delivery may be established when the transaction occurs in the first location. The time associated with the delivery may be a time window during which the delivery should occur. The time may be the latest time threshold before which the delivery needs to be completed. For example, some items such as milk or produce may spoil after a particular amount of time so the delivery needs to be completed before expiration of a time window. The time may be the earliest possible time that the delivery may occur. For example, a person ordering an item may be out of town and want the delivery only after they plan to return.

Figure 7:
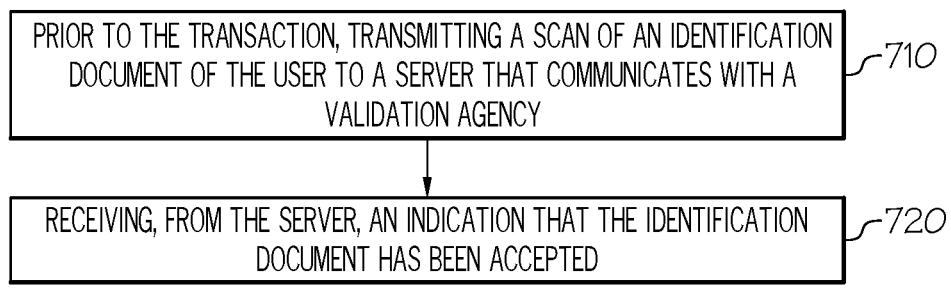

FIG. 7 is a flowchart of operations according to some embodiments of the present inventive concepts. Referring now to FIG. 7, an account and/or profile may be established with a vendor or supplier by a user. The profile may include user preferences and identification documentation that help establish biometric authentication. The account and/or profile may be set up before a user begins a transaction. Prior to a transaction, a scan of an identification document of the user may be transmitted to a server that communicates with a validation agency, at block 710. The user device may receive, from the server, an indication that the identification document has been accepted, at block 720. The server may store information related to the identification document in a database for future reference. Identification documents may include a driver's license, employer badge, passport, etc. The server may communicate with a validation agency or government agency to verify the authenticity of the identification document. In some embodiments, the server may validate the identification document by recognizing portions of a scan or an image of the identification document. Portions of the identification document used for validation may include watermarks, optical recognition, embedded marking, serial numbers, spectroscopic color scanning, and/or other symbols in the identification document. Upon verification of the validity of the identification document, biometric information may be collected from the user. The biometric information may then be associated with the identification document and securely stored in a database and/or at the vendor server. Once the identification process is completed, the user may be designated as a valid user that can participate in transactions.

FIG. 8 is a flowchart of operations according to some embodiments of the present inventive concepts. Referring now to FIG. 8, responsive to the indication that the identification document has been accepted, biometric identification information of the user may be transmitted for storing at the server, at block 810. This biometric identification information is used for authenticating the first user and/or for authenticating the second user. The biometric identification information is requested by the server from the terminal after the identification document has been verified. Upon receiving confirmation that the identification document has been accepted by the server or a request for biometric information from the server, the user may then provide biometric information which is transmitted from the terminal to the server for storage in a database associated with the server.

FIG. 9 is a flowchart of operations according to some embodiments of the present inventive concepts. Referring now to FIG. 9, it may be determined that the second user at the second location is different from the first user at the first location, at block 910. The first user who initiated the transaction may have asked an authorized recipient to pick up the item or accept delivery of the item at the second location. At the time of the transaction or following the initiating of the transaction for the item, the first user may have an opportunity to designate an authorized recipient for the item. The server may determine if the second user is an authorized recipient designated by the first user, at block 920. Responsive to determining that the second user is the authorized recipient designated by the first user, the server may authorize access to the item by the second user at the second location, at block 930. The server may send an access authorization indication to the terminal associated with the delivery representative. Upon receiving authorization for delivery to the designated user, the delivery representative may then provide the item.

FIG. 10 is a flowchart of operations according to some embodiments of the present inventive concepts. Referring now to FIG. 10, according to some embodiments, the terminal at the second location (i.e., the delivery location) may receive an indication from the first user indicating an identification of the second user as the authorized recipient, at block 1010. In order to prevent fraud, the first user may be required to provide biometric authentication information to verify their identity before designating an authorized recipient. The biometric authentication and the authorized recipient information may be transmitted to a server. If the biometric authentication information is valid, the authorized recipient information may be stored in the database for later usage for delivery.

Figure 11:
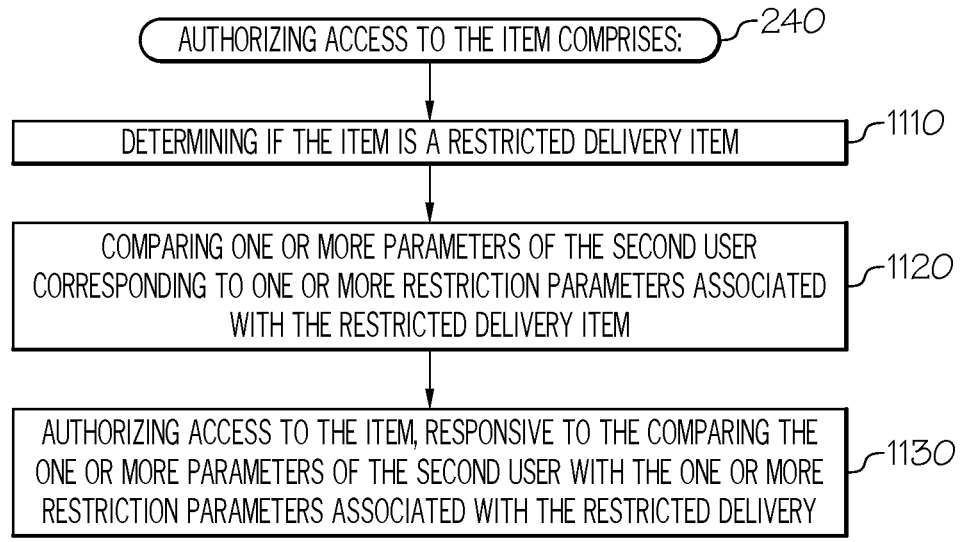

FIG. 11 is a flowchart of operations according to some embodiments of the present inventive concepts. Referring now to FIG. 11, authorizing access to the item may include determining if the item is a restricted delivery item, at block 1110. Restricted delivery items may have restrictions on delivery such as the age of the recipient, legal status of the recipient, time of delivery, amount of an item allowed to be delivered, etc. For example, there may be limit on the amount of alcohol or cigarettes that are allowed to be delivered to a particular user in a single transaction or collectively over a time period. The recipient may be required to be a legal adult (such as age 18) or the minimum legal drinking age (such as age 21). Some items may not be legally delivered to some locations that are jurisdictions with restrictions or bans on the sale/delivery of particular items. If an item is a restricted delivery item, one or more parameters of the second user that would receive the delivery may be compared to one or more restriction parameters associated with the restricted delivery item, at block 1120. For example, the age of the user in the profile may be compared with the age requirements associated with the item. Based on the comparison of these parameters of the user who is attempting to receive delivery with the restriction parameters associated with the restricted delivery item, access to the item may be authorized or denied, at block 1130.

According to some embodiments, delivery of the item may be authorized if the second location of the second user is within a predetermined proximity of a delivery location established at a time of the transaction. For example, if the second user is in a nearby building as the delivery address (i.e., within a predetermined distance), then delivery of the item may be authorized such that the delivery representative may leave the package near the building. In some embodiments, the delivery of the item may be authorized for a specific time window, such as during the business day.

Figure 12:
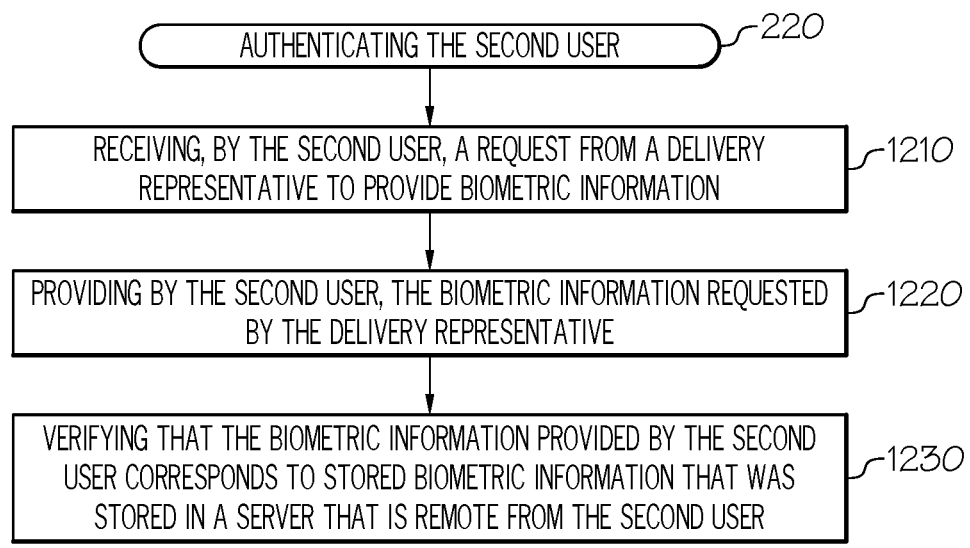

FIG. 12 is a flowchart of operations according to some embodiments of the present inventive concepts. Referring now to FIG. 12, authenticating the second user may include receiving, by the second user, a request from a delivery representative or associated device to provide biometric information, at block 1210. The second user may provide the biometric information requested by the delivery representative, at block 1220. The biometric information provided by the second user may be verified to make sure that it corresponds to stored biometric information that was stored in a server that is remote from the second user, at block 1230.

FIG. 13 and FIG. 14 are flowcharts of operations according to some embodiments of the present inventive concepts. Referring now to FIG. 13, there may be cases where the first user (i.e., the user that initiated the transaction at the first location) is the same as the second user that is at the second location. During the transaction by the user at the first location, a certificate associated with the transaction and biometric information of the user may be stored in a database, at block 1310. The certificate may indicate that the user received a vaccination or may authorize a prescription for a medicine. The certificate is protected by the biometric information that must be validated before accepting the certificate at a different location. Referring now to FIG. 14, the certificate and the biometric information of the first user may be retrieved from the database, when the user attempts to authenticate at the second location (i.e., a different location), at block 1410. A verification operation may take place to determine if the biometric information of the first user from the database matches with biometric information of the first user collected at the second location, at block 1420. Responsive to verifying that the biometric information of the first user from the database matches with biometric information of the first user collected at the second location, access to the certificate may be provide, at block 1430. Access to the certificate may provide, for example, an indication that a vaccination was previously received by the user or that the user is authorized to receive a prescription medication. In other words, the certificate may indicate a proof of vaccination, a prescription for a medication, and/or an authorization to carry a medication.

FIG. 15 is a flowchart of operations according to some embodiments of the present inventive concepts. Referring now to FIG. 15, a cost of the item may be determined based on the second location associated with delivery of the item, at block 1510. The cost may be based on tax laws associated with the delivery location, tariffs, or duty-free allowances. The cost may be based on the speed of delivery, time of delivery or other delivery constraints. The cost may be provided to the first user upon delivery of the item, at block 1520.

Figure 16:
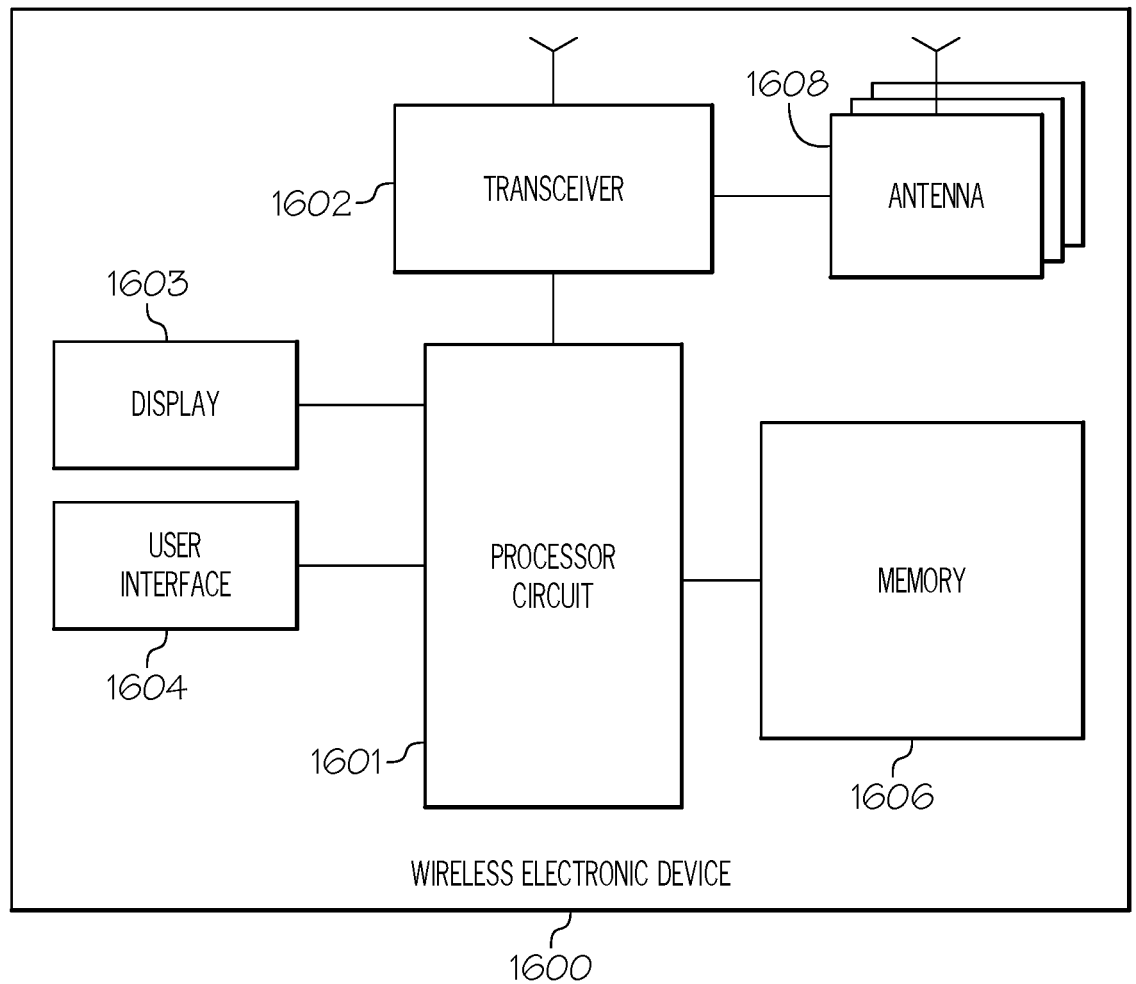
FIG. 16 is a block diagram of a wireless electronic device, according to various embodiments described herein.

FIG. 16 is a block diagram of a wireless electronic device 1600 of an authentication system, such as system 100 of FIG. 1. The wireless electronic device 1600 of FIG. 16 may correspond to devices such as terminals 120, 170, and/or 190 of FIG. 1. The wireless electronic device 1600 may be integrated with a camera and/or sensors such as biometric sensors and is configured to perform operations according to one or more embodiments disclosed herein. Referring to FIG. 16, wireless electronic device 1600 includes a display 1603, a processor circuit 1601, and a memory 1606 containing computer readable program code. Display 1603 may include a display circuit, display driver, and/or a screen for display/viewing of information or images. The processor circuit 1601 may include one or more data processing circuits, such as a general purpose and/or special purpose processor, e.g., microprocessor and/or digital signal processor, which may be co-located or distributed across one or more networks. The processor circuit 1601 is configured to execute the computer readable program code in the memory 1606 to perform at least some of the operations and methods of described herein as being performed by the wireless electronic device 1600. A user interface 1604 is coupled to the processor circuit 1601 and may communicate with a server or other external network entity, directly or indirectly.

The wireless electronic device 1600 may be configured to perform operations described herein related to the mobile device and/or terminal. Some embodiments of the present inventive concepts may be directed to a computer program product that includes a non-transitory computer readable storage medium including computer readable program code therein that when executed by a processor causes the processor to perform operations described herein.

Still referring to FIG. 16, the wireless electronic device 1600 may include a transceiver 1602 configured to perform various operations such as receiving first biometric information of a user located at a first location corresponding to a transaction location associated with the item. The wireless electronic device 1600 may receive second biometric information of the user located at a second location corresponding to a delivery location.

A server that is remote from the wireless electronic device 1600 may include a one or more processors configured to perform operations including verifying that the first biometric information of the user at the first location corresponds to the second biometric information of the user at the second location, and authorizing access to the item at the second location, responsive to verifying that first biometric information corresponds to the second biometric information. In some embodiments, the verification and the authorization of access to the item may be performed by the wireless electronic device 1600.

According to some embodiments, a system may include a server, a first wireless electronic device that includes a first processor configured to collect first biometric information of a user located at a first location for a transaction associated with an item, and a first transceiver configured to transmit the first biometric information from the wireless electronic device to the server. The system may include a second wireless electronic device that includes a second processor configured to collect second biometric information of the user located at a second location that is different from the first location, and a second transceiver configured to transmit the second biometric information from the wireless electronic device to the server. The server in the system may be configured to perform operations such as verifying that the first biometric information of the user at the first location corresponds to the second biometric information of the user at the second location, and authorizing access to the item at the second location, responsive to verifying that first biometric information corresponds to the second biometric information.

Figure 17:
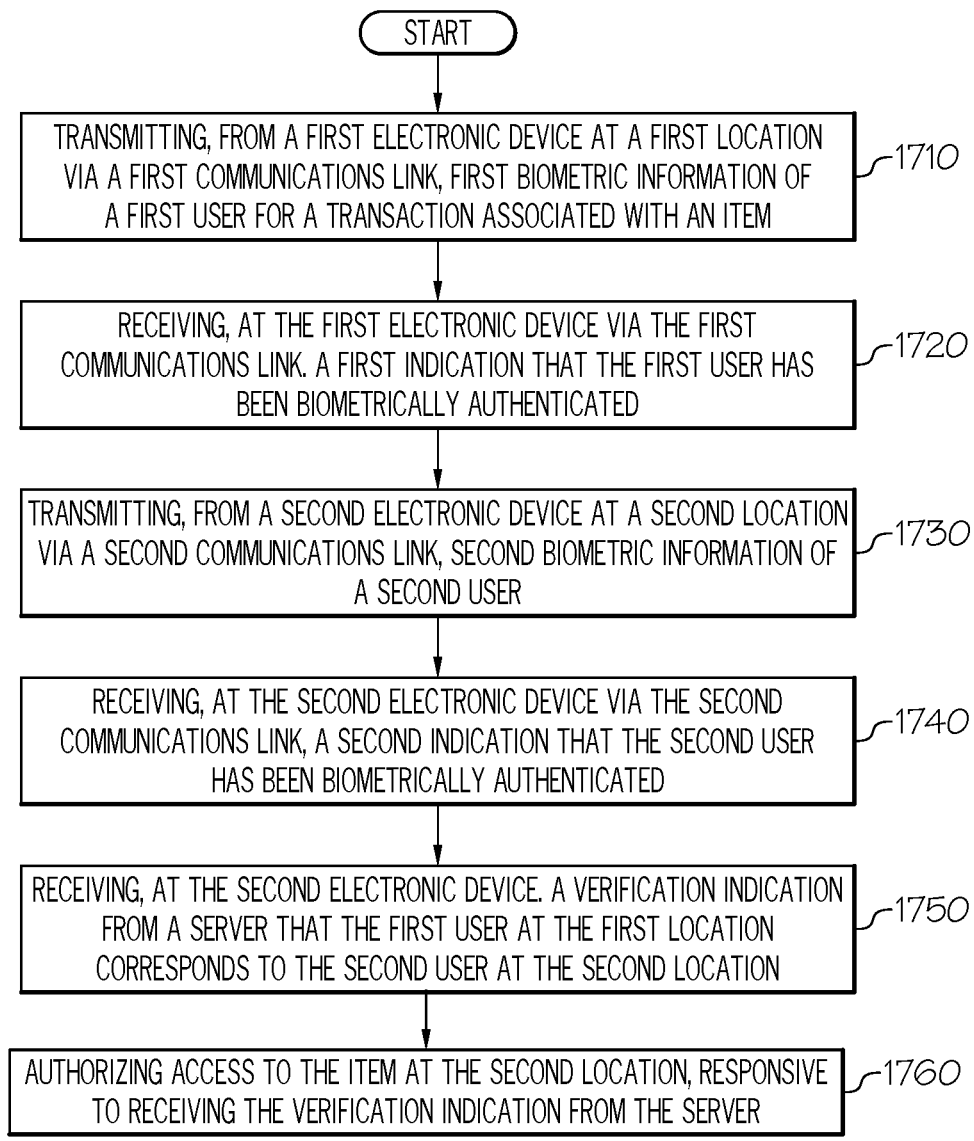
FIG. 17 is a flowchart of operations for authenticating a user in a the system of FIG. 1, according to various embodiments described herein.

FIG. 17 is a flowchart of operations for authenticating a user in a the system of FIG. 1, according to various embodiments described herein. Referring to FIG. 17, first biometric information of a first user for a transaction associated with an item may be transmitted from a first electronic device at a first location via a first communications link, at block 1710. The communication link may be a link over a network from the first electronic device to a server. The server may compare the received biometric information with previously stored biometric information in a profile of the user and determine the validity of the user. In other words, the user may be securely identified and/or authenticated based on the biometric information. A first indication that the first user has been biometrically authenticated, may be received at the first electronic device via the first communications link, at block 1720. Second biometric information of a second user may be transmitted from a second electronic device at a second location via a second communications link, at block 1730. The second communication link may connect the second electronic device over a network to the same server as the first electronic device. A second indication that the second user has been biometrically authenticated may be received at the second electronic device via the second communications link, at block 1740. A verification indication from a server that the first user at the first location corresponds to the second user at the second location may be received at the second electronic device, at block 1750. Access to the item at the second location may be authorized, responsive to receiving the verification indication from the server, at block 1760. In some embodiments, the verification indication and an indication authorizing delivery of the item may be transmitted together from the server to the second electronic device. The second electronic device may be a mobile device belonging to the user or a terminal associated with the delivery representative. In some embodiments, the second biometric information may be sent from the second user's device to the server. The verification indication and/or the authorization for delivery may be transmitted over a communication link on a network from the server to a terminal associated with the delivery representative.

FURTHER EMBODIMENTS

In the above-description of various embodiments of the present disclosure, it is to be understood that the terminology used herein is for the purpose of describing particular embodiments only and is not intended to be limiting of the invention. Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of this specification and the relevant art, and will not be interpreted in an idealized or overly formal sense unless expressly so defined herein.

When an element is referred to as being "connected", "coupled", "responsive", or variants thereof to another element, it can be directly connected, coupled, or responsive to the other element or intervening elements may be present. In contrast, when an element is referred to as being "directly connected", "directly coupled", "directly responsive", or variants thereof to another element, there are no intervening elements present. Like numbers refer to like elements throughout. Furthermore, "coupled", "connected", "responsive", or variants thereof as used herein may include wirelessly coupled, connected, or responsive. As used herein, the singular forms "a", "an" and "the" are intended to include the plural forms as well, unless the context clearly indicates otherwise. Well-known functions or constructions may not be described in detail for brevity and/or clarity. The term "and/or" includes any and all combinations of one or more of the associated listed items.

It will be understood that, although the terms first, second, third, etc. may be used herein to describe various elements, and elements should not be limited by these terms; rather, these terms are only used to distinguish one element from another element. Thus, a first element discussed could be termed a second element without departing from the scope of the present inventive concepts.

As used herein, the terms "comprise", "comprising", "comprises", "include", "including", "includes", "have", "has", "having", or variants thereof are open-ended, and include one or more stated features, integers, elements, steps, components or functions but does not preclude the presence or addition of one or more other features, integers, elements, steps, components, functions or groups thereof.

Example embodiments are described herein with reference to block diagrams and/or flowchart illustrations of computer-implemented methods, apparatus (systems and/or devices) and/or computer program products. It is understood that a block of the block diagrams and/or flowchart illustrations, and combinations of blocks in the block diagrams and/or flowchart illustrations, can be implemented by computer program instructions that are performed by one or more computer circuits. These computer program instructions may be provided to a processor circuit of a general purpose computer circuit, special purpose computer circuit, and/or other programmable data processing circuit to produce a machine, such that the instructions, which execute via the processor of the computer and/or other programmable data processing apparatus, transform and control transistors, values stored in memory locations, and other hardware components within such circuitry to implement the functions/acts specified in the block diagrams and/or flowchart block or blocks, and thereby create means (functionality) and/or structure for implementing the functions/acts specified in the block diagrams and/or flowchart block(s).

These computer program instructions may also be stored in a tangible computer-readable medium that can direct a computer or other programmable data processing apparatus to function in a particular manner, such that the instructions stored in the computer-readable medium produce an article of manufacture including instructions which implement the functions/acts specified in the block diagrams and/or flowchart block or blocks.

A tangible, non-transitory computer-readable medium may include an electronic, magnetic, optical, electromagnetic, or semiconductor data storage system, apparatus, or device. More specific examples of the computer-readable medium would include the following: a portable computer diskette, a random access memory (RAM) circuit, a read-only memory (ROM) circuit, an erasable programmable read-only memory (EPROM or Flash memory) circuit, a portable compact disc read-only memory (CD-ROM), and a portable digital video disc read-only memory (DVD/Blu-ray).

The computer program instructions may also be loaded onto a computer and/or other programmable data processing apparatus to cause a series of operational steps to be performed on the computer and/or other programmable apparatus to produce a computer-implemented process such that the instructions which execute on the computer or other programmable apparatus provide steps for implementing the functions/acts specified in the block diagrams and/or flowchart block or blocks. Accordingly, embodiments of the present disclosure may be embodied in hardware and/or in software (including firmware, resident software, microcode, etc.) that runs on a processor such as a digital signal processor, which may collectively be referred to as "circuitry," "a module" or variants thereof.

Aspects of the present disclosure are described herein with reference to flowchart illustrations and/or block diagrams of methods, apparatus (systems), and computer program products according to embodiments of the disclosure. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable instruction execution apparatus, create a mechanism for implementing the functions/acts specified in the flowchart and/or block diagram block or blocks.

These computer program instructions may also be stored in a computer readable medium that when executed can direct a computer, other programmable data processing apparatus, or other devices to function in a particular manner, such that the instructions when stored in the computer readable medium produce an article of manufacture including instructions which when executed, cause a computer to implement the function/act specified in the flowchart and/or block diagram block or blocks. The computer program instructions may also be loaded onto a computer, other programmable instruction execution apparatus, or other devices to cause a series of operational steps to be performed on the computer, other programmable apparatuses or other devices to produce a computer implemented process such that the instructions which execute on the computer or other programmable apparatus provide processes for implementing the functions/acts specified in the flowchart and/or block diagram block or blocks.

The flowcharts and block diagrams in the figures illustrate the architecture, functionality, and operation of possible implementations of systems, methods, and computer program products according to various aspects of the present disclosure. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

It should also be noted that in some alternate implementations, the functions/acts noted in the blocks may occur out of the order noted in the flowcharts. For example, two blocks shown in succession may in fact be executed substantially concurrently or the blocks may sometimes be executed in the reverse order, depending upon the functionality/acts involved. Moreover, the functionality of a given block of the flowcharts and/or block diagrams may be separated into multiple blocks and/or the functionality of two or more blocks of the flowcharts and/or block diagrams may be at least partially integrated. Finally, other blocks may be added/inserted between the blocks that are illustrated. Moreover, although some of the diagrams include arrows on communication paths to show a primary direction of communication, it is to be understood that communication may occur in the opposite direction to the depicted arrows.

Many different embodiments have been disclosed herein, in connection with the above description and the drawings. It will be understood that it would be unduly repetitious and obfuscating to literally describe and illustrate every combination and subcombination of these embodiments. Accordingly, the present specification, including the drawings, shall be construed to constitute a complete written description of various example combinations and subcombinations of embodiments and of the manner and process of making and using them, and shall support claims to any such combination or subcombination. Many variations and modifications can be made to the embodiments without substantially departing from the principles described herein. All such variations and modifications are intended to be included herein within the scope.

The invention claimed is:

1. A method for authenticating a user, the method comprising:

transmitting, from a first electronic device at a first location via a first communications link, first biometric information of a first user;

authenticating a first identity of the first user for a transaction associated with an item;

transmitting, from a second electronic device at a second location via a second communications link, second biometric information of a second user;

authenticating a second identity of the second user located at the second location that is different from the first location;

verifying, by a server, that the first user at the first location corresponds to the second user at the second location;

authorizing access to the item at the second location, responsive to verifying by the server that the first user at the first location corresponds to the second user at the second location;

storing, in a database associated with the server, a certificate associated with the transaction, location information, and biometric information of the first user associated with the transaction, responsive to initiating the transaction by the first user, wherein the location information indicates where the biometric information of the user was collected;

retrieving, by the server, the certificate and the biometric information of the first user from the database, when the first user attempts to authenticate at the second location;

verifying, by the server, whether the biometric information of the first user from the database matches with biometric information of the second user collected at the second location;

validating the location information to determine that the biometric information was obtained at a valid facility; and providing, by the server, access to the certificate, responsive to verifying that the biometric information of the first user from the database matches with biometric information of the second user collected at the second location.

2. The method for authenticating the user of claim 1, wherein the authenticating the first user comprises comparing, by the server, the first biometric information of the first user with first stored biometric information associated with the first user, and wherein the authenticating the second user comprises comparing, by the server, the second biometric information of the second user with second stored biometric information associated with the second user.

3. The method of authenticating the user of claim 2, wherein the first biometric information and the second biometric information each comprise one or more of fingerprinting, retina scanning, iris recognition, facial recognition, voice identification, or finger vein identification.

4. The method for authenticating the user of claim 1, wherein the verifying comprises:

determining that first authentication information associated with the first user corresponds to second authentication information associated with the second user; and identifying that the second user is same as the first user, responsive to the first authentication information corresponding to the second authentication information.

5. The method of authenticating the user of claim 1, further comprising:

determining that the second location corresponds to a delivery location established at a time of the transaction; and delivering the item to the delivery location, responsive to the authorizing access to the item.

6. The method of authenticating the user of claim 1, further comprising:
prior to the transaction, transmitting a scan of an identification document of the user to a server that communicates with a validation agency; and
receiving, from the server, an indication that the identification document has been accepted.

7. The method of authenticating the user of claim 6, further comprising:
transmitting, responsive to the indication that the identification document being accepted, biometric identification information of the user for storing at the server, wherein the biometric identification information is used for authenticating the first user and/or for authenticating the second user.

8. The method of authenticating the user of claim 1, further comprising:
determining that the second user at the second location is different from the first user at the first location;
determining if the second user is an authorized recipient designated by the first user; and
authorizing access to the item by the second user at the second location, responsive to determining that the second user is the authorized recipient designated by the first user.

9. The method for authenticating the user of claim 8, further comprising:
receiving an indication from the first user indicating an identification of the second user as the authorized recipient.

10. The method of authenticating the user of claim 1, wherein the authorizing access to the item comprises:
determining if the item is a restricted delivery item;
comparing one or more parameters of the second user corresponding to one or more restriction parameters associated with the restricted delivery item; and
authorizing access to the item, responsive to the comparing the one or more parameters of the second user with the one or more restriction parameters associated with the restricted delivery item.

11. The method of authenticating the user of claim 1, wherein delivery of the item is authorized if the second location of the second user is within a predetermined proximity of a delivery location established at a time of the transaction.

12. The method of authenticating the user of claim 11, wherein the delivery of the item is authorized for a specific time window.

13. The method of authenticating the user of claim 1, wherein the authenticating the second user comprises:
receiving, by the second user, a request from a delivery representative to provide biometric information;
providing by the second user, the biometric information requested by the delivery representative; and
verifying that the biometric information provided by the second user corresponds to stored biometric information that was stored in a server that is remote from the second user.

14. The method of authenticating the user of claim 1, wherein the certificate comprises a proof of vaccination and/or an authorization to carry a medication.

15. The method of authenticating the user of claim 1, further comprising:
determining a cost of the item based on the second location associated with delivery of the item; and
providing the cost to the first user upon delivery of the item.

16. A wireless electronic device configured to perform the method of claim 1.

17. A computer program product comprising:
a non-transitory computer readable storage medium comprising computer readable program code therein that when executed by a processor causes the processor to perform operations of the method of claim 1.

18. A wireless electronic device for authenticating a delivery of an item, the wireless electronic device comprising:
a transceiver configured to perform operations comprising:
receiving second biometric information of a user located at a delivery location;
transmitting, to a server, the second biometric information of the user; and
receiving, from the server, a certificate associated with a transaction of the item, location information, and biometric information of the user associated with the transaction, responsive to verifying that first biometric information of the user from a database matches with the second biometric information of the user collected at the delivery location, and responsive to validating the location information to determine that the biometric information was obtained at a valid facility, wherein the certificate was stored in a database associated with the server responsive to initiation of the transaction by the user, and wherein the location information indicates where the biometric information of the user was collected; and
one or more processors configured to perform operations comprising:
authorizing access to the item at the delivery location, responsive to receiving the certificate.

19. A system comprising:
a server;
a first wireless electronic device comprising:
a first processor configured to collect first biometric information of a user located at a first location for a transaction associated with an item; and
a first transceiver configured to transmit the first biometric information from the first wireless electronic device to the server;
a second wireless electronic device comprising:
a second processor configured to collect second biometric information of the user located at a second location that is different from the first location; and
a second transceiver configured to transmit the second biometric information from the second wireless electronic device to the server;
wherein the server is configured to perform operations comprising:
verifying that the first biometric information of the user at the first location corresponds to the second biometric information of the user at the second location;
authorizing access to the item at the second location, responsive to verifying that first biometric information corresponds to the second biometric information;
storing, in a database associated with the server, a certificate associated with the transaction, location information, and biometric information of the first user associated with the transaction, responsive to initiating the transaction by the first user, wherein the location information indicates where the biometric information of the user was collected;

retrieving, by the server, the certificate and the biometric information of the user from the database, when the user attempts to authenticate at the second location;

verifying, by the server, whether the biometric information of the user from the database matches with biometric information of the user collected at the second location;

validating the location information to determine that the biometric information was obtained at a valid facility; and providing, by the server, access to the certificate, responsive to verifying that the biometric information of the user from the database matches with the biometric information of the user collected at the second location.

20. A method for authenticating a user, the method comprising:

transmitting, from a first electronic device at a first location via a first communications link, first biometric information of a first user for a transaction associated with an item, wherein first location information indicating the first location is stored with the first biometric information in a database associated with a server;

receiving, at the first electronic device via the first communications link, a first indication that the first user has been biometrically authenticated;

transmitting, from a second electronic device at a second location via a second communications link, second biometric information of a second user;

receiving, at the second electronic device via the second communications link, a second indication that the second user has been biometrically authenticated;

receiving, at the second electronic device, a verification indication from the server that the first user at the first location corresponds to the second user at the second location;

determining whether the item is a restricted delivery item comprising a restriction on delivery of the item based on one or more of an age of the second user, legal status of the second user, time of delivery, or an amount of the item allowed to be delivered;

comparing one or more parameters of the second user with one or more restriction parameters associated with the restricted delivery item; and authorizing access to the item at the second location, responsive to the comparing the one or more parameters of the second user with the one or more restriction parameters associated with the restricted delivery item.

* * * * *